United States Patent
Igaue et al.

(10) Patent No.: US 6,264,644 B1
(45) Date of Patent: *Jul. 24, 2001

(54) DISPOSABLE BODY FLUID ABSORBENT ARTICLE HAVING DISPOSABLE SECURING MEANS

(75) Inventors: Takamitsu Igaue, Ehime-ken; Hiroyuki Soga, Kagawa-ken, both of (JP)

(73) Assignee: Uni-Charm Corporation, Ehime-Ken (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/917,928

(22) Filed: Aug. 27, 1997

(30) Foreign Application Priority Data

Aug. 30, 1996 (JP) .................................................... 8-229603

(51) Int. Cl.⁷ .................................................... A61F 13/15
(52) U.S. Cl. ............................ 604/389; 604/390; 604/396
(58) Field of Search ................................ 604/385.1, 386, 604/389–391, 393–396, 385.13

(56) References Cited

U.S. PATENT DOCUMENTS

| | | | |
|---|---|---|---|
| 4,047,528 | * 9/1977 | Karami | 604/390 |
| 4,207,895 | * 6/1980 | Schaar | 604/390 |
| 4,516,976 | * 5/1985 | Bell | 604/389 |
| 4,869,724 | * 9/1989 | Scripps | 604/391 |

FOREIGN PATENT DOCUMENTS

| | | | |
|---|---|---|---|
| 0 314 535 | 5/1989 | (EP) . | |
| 0 338 680 | 10/1989 | (EP) . | |
| 6623330 | * 11/1994 | (EP) | 604/389 |
| 58-22908 | 2/1983 | (JP) . | |
| 94 09736 | 5/1994 | (WO) . | |

* cited by examiner

Primary Examiner—Aaron J. Lewis
Assistant Examiner—K. M. Reichle
(74) Attorney, Agent, or Firm—Lowe Hauptman Gilman & Berner, LLP

(57) ABSTRACT

A disposal tape securing arrangement used to secure a disposable body fluid absorbent article such as a disposable diaper in a rolled up state for disposal includes an adhesive tape and a release tape. The adhesive tape is fixed at one end portion to the outer surface of the article and has an adhesive zone on the opposite end portion (i.e., free end portion). The release tape extends in alignment with the adhesive tape and has a release portion fixed to the outer surface of the article and a fold-back portion being contiguous to the release portion and folded back adjacent the end of the adhesive tape. The adhesive zone provided on the adhesive tape is releasably bonded to the release portion and the fold-back portion of the release tape is fixed to the inner surface of the free end portion of the adhesive tape.

7 Claims, 2 Drawing Sheets

DISPOSABLE BODY FLUID ABSORBENT ARTICLE HAVING DISPOSABLE SECURING MEANS

BACKGROUND OF THE INVENTION

This invention relates generally to disposable body fluid absorbent articles such as disposable diapers, sanitary napkin or incontinent pants and more particularly to such articles provided with means used to secure such articles in a state convenient for disposal thereof.

Japanese Laid-Open Utility Model Application No. Sho5822908discloses a disposable diaper provided with an adhesive tape used to secure the used diaper in a rolled up or folded state to prevent any stained portion of the diaper from being exposed. Therefore, the used diaper can be disposed of in a manner which is not only sightly but also sanitary.

The foregoing adhesive tape has its inner surface applied with adhesive by means of which one end portion (fixed end portion) of the adhesive tape is fixed to the outer surface of a backsheet of the diaper and the opposite end portion defines a free end portion. The used diaper can be maintained in a rolled up or folded state by bonding the free end portion of the adhesive to the diaper at an appropriate location.

With the foregoing adhesive tape, a shear stress is generated between the adhesive tape and the backsheet as the adhesive tape is linearly pulled in the direction from the fixed end portion toward the free end portion. According to this prior art, the adhesive is selected so that the shear stress does not peel the fixed end portion off from the backsheet. However, when the free end portion of the adhesive is pulled so as to be folded back toward the fixed end portion, a peeling force is generated between the fixed end portion and the backsheet. As a result, the fixed end portion is easily peeled off from the backsheet or the backsheet is broken in the proximity of the fixed end portion. Such undesirable situation may often occur, for example, when a baby wearing the diaper plays with the adhesive tape.

SUMMARY OF THE INVENTION

In view of the problem as has been mentioned above, it is a principal object of the invention to improve a disposable body fluid absorbent article provided with an adhesive tape used to secure the article prior to disposal of the article so that the adhesive tape cannot be easily peeled off from the article.

The object set forth above is achieved, according to the invention, by a disposable body fluid absorbent article comprising an inner surface intended to be placed adjacent a wearer's skin, an outer surface intended to be placed remotely from the wearer's skin and disposal securing means used to secure said article in a shape desired for disposal of said article, wherein:

said disposal securing means comprise a first tape and a second tape disposed between said first tape and the outer surface of the article and extending in alignment with said first tape;

said first tape has inner and outer surfaces and comprises a first fixed portion extending adjacent longitudinally one end and fixed on the inner surface of said first tape to the outer surface of said article and a free portion extending adjacent the longitudinally opposite end, said free portion comprising, as viewed from said longitudinally opposite end toward said first fixed portion, a tab zone having no adhesive on both the inner and outer surfaces of said first tape and an adhesive zone having adhesive on the inner surface of said first tape alone;

said second tape has inner and outer surfaces and comprises a second fixed portion extending from said free portion toward said first fixed portion of said first tape and fixed on the inner surface of said second tape to the outer surface of said article and a fold-back portion being contiguous to said second fixed portion and folded back adjacent said first fixed portion of said first tape with the inner surface of said second tape facing outward; and said adhesive zone provided on said free portion of said first tape is bonded to the outer surface of said second fixed portion of said second tape and said fold-back portion of said second tape is fixed on the outward facing surface of said fold-back portion to the inner surface of said free portion of said first tape.

In the article according to the invention, the disposal securing means for this article after use comprises the adhesive tape and the release tape. The adhesive tape is fixed at its one end to the outer surface of the article and the release tape has the fold-back portion fixed to the inner surface of the adhesive tape at the location in the proximity of said one end. When a tension is exerted to the adhesive tape, substantially no peeling force is exerted to the end of the adhesive tape at which the adhesive tape is fixed to the outer surface of the garment. In this manner, the adhesive tape is not readily peeled off from the article.

Other and further objects, features and advantages of the invention will appear more fully from the following description.

DESCRIPTION OF THE PREFERRED EMBODIMENT

Figure 1:
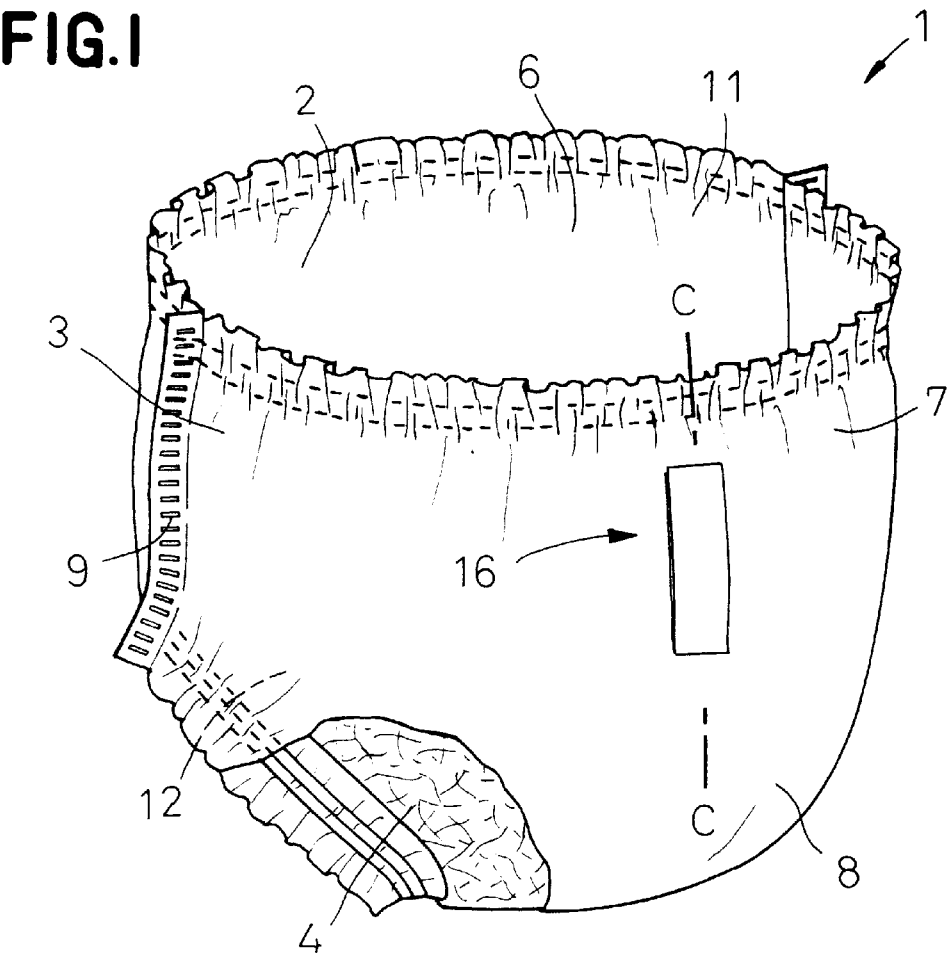
FIG. 1 is a perspective view showing a disposable diaper according to the invention as partially broken away.

A pull-on diaper 1 shown in FIG. 1 in a perspective view as partially broken away comprises a liquid-permeable topsheet 2 formed by a nonwoven fabric made of thermoplastic synthetic fibers, a liquid-impermeable backsheet 3 formed by a thermoplastic synthetic resin film and a liquid-absorbent core 4 disposed between these two sheets 2, 3. The diaper 1 has a front waist region 6, a rear waist region 7 and a crotch region 8 extending between these two regions 6, 7. The topsheet 2 and the backsheet 3 are joined to each other by means of hot melt adhesives (not shown) at their portions extending outward beyond a peripheral edge of the absorbent core 4. The front and rear waist regions 6, 7 have their transversely opposite side edges put flat together and welded to each other at spots 9 intermittently arranged in their vertical directions so as to define a waist-opening 11 and a pair of leg-openings 12. The rear waist region 7 is provided on a center line 2—2 dividing this waist region 7 in right and left halves with disposal securing means 16 used to secure the used diaper 1 in a rolled up or folded state for disposal thereof.

Figure 2:
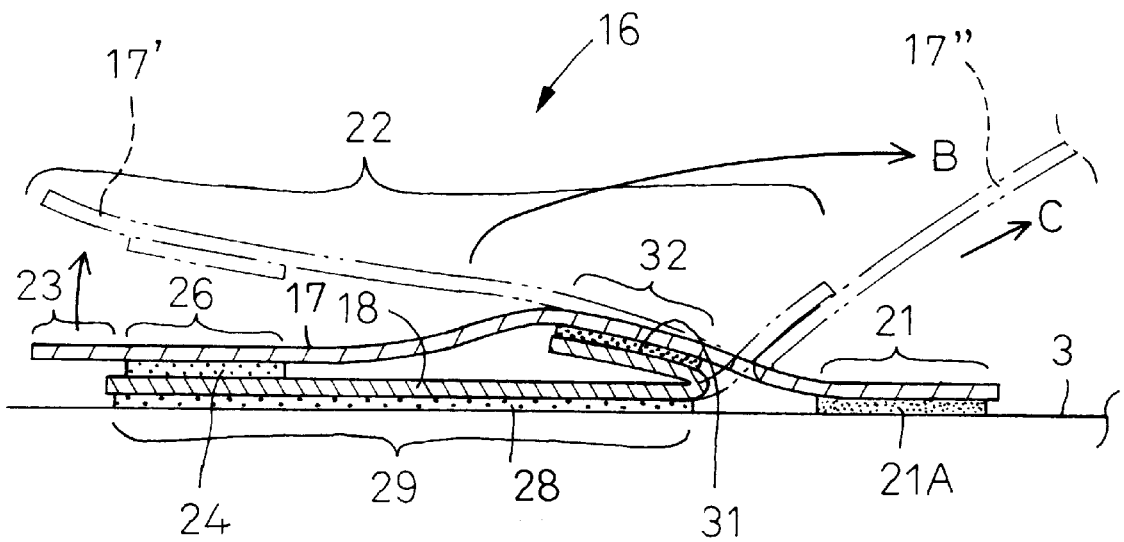
FIG. 2 is a fragmentary sectional view taken along a line 2—2 in FIG. 1.

FIG. 2 is a sectional view taken along line 2—2 in FIG. 1, showing the disposal securing means 16. The disposal securing means 16 comprises an adhesive tape 17 and a release tape 18. The adhesive tape 17 extends vertically of the diaper 1 and has a backward portion 21 adjacent the crotch region 8. An inner surface of the backward portion 21 is applied with adhesive 21A by which the backward portion 21 is fixed to the outer surface of the backsheet 3. On the side opposite to the backward portion 21, the adhesive tape 17 has a freely deformable forward portion 22 comprising, from its upper tip toward the backward portion 21, a tab zone 23 which is non-adhesive on both its inner and outer surfaces and an adhesive zone 26 which is contiguous to the tab zone 23 and applied on its inner surface with adhesive 24. While an area extending between the adhesive zone 26 and the backward portion 21 is shown as applied with no adhesive, this area may be applied with adhesive 24, if desired.

The release tape 18 extends vertically of the diaper 1 in alignment with the adhesive tape 17. The release tape 18 comprises a release portion 29 fixed to the outer surface of the backsheet 3 by means of adhesive 28 applied on the inner surface of the release portion 29 and a fold-back portion 32. The fold-back portion 32 is contiguous to the release portion 29 and folded back onto the release portion 29 and fixed to the inner surface of the adhesive tape 17 by means of adhesive 31. The adhesive tape 17 is releasably bonded to the outer surface of the release portion 29 by means of the adhesive zone 26. To make the adhesive tape 17 releasable from the release portion 29, the outer surface of the release portion 29 may be applied with a release agent or may be finely embossed. While it is preferred to employ an inelastic tape material for the adhesive tape 17, it is also possible to employ an elastic tape material.

Figure 3:
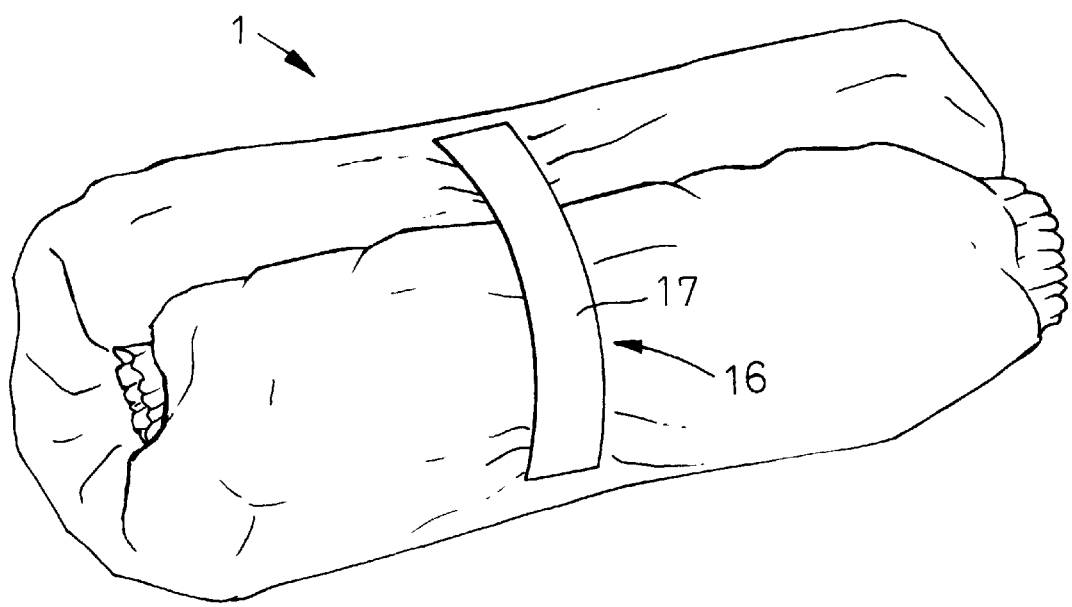
FIG. 3 is a perspective view of the diaper as rolled up.

FIG. 3 is a perspective view showing the diaper 1 as secured in a rolled up state using the disposal securing means 16 for disposal of the used diaper 1. The used diaper 1 is rolled up in its vertical direction and maintained in this state by the adhesive tape 17 so as to prevent any stained portions of the used diaper from being exposed. Such manner of securing the used diaper for disposal is preferable not only to look at but also from a sanitary viewpoint.

The disposal securing means 16 may be effectively used by peeling the adhesive tape 17 off from the release tape 18 with the tab zone 23 held by the user's fingers, as shown by imaginary lines 17' in FIG. 2, and then by bonding the adhesive zone 26 to the rolled up diaper 1 at an appropriate location. During such series of operation, the adhesive tape 17 may be excessively pulled toward the crotch region 8 (i.e., rightward as viewed in FIG. 2) as indicated by arrows B and C in FIG. 2 and temporarily unfolded to a position shown by imaginary lines 17". Such situation may occur also when a baby wearing the diaper 1 plays with the adhesive tape 17. However, such undesirable situation can be compensated by a unique arrangement of the inventive diaper 1. More specifically, the fold-back portion 32 of the release tape 18 is also pulled and unfolded in the direction as indicated by the arrow C as the adhesive tape 17 is pulled and unfolded in the direction as indicated by the arrow C. During this concurrent movement of the adhesive tape 17 and the fold-back portion 32, a tension is exerted only upon the release tape 18 but not upon the backward portion 21 of the adhesive tape 17. Such arrangement allows the adhesive tape 17 to be free from a peeling force which would otherwise be exerted thereupon and thereby prevents the adhesive tape 17 from being easily peeled off from the diaper 1.

Figure 4:
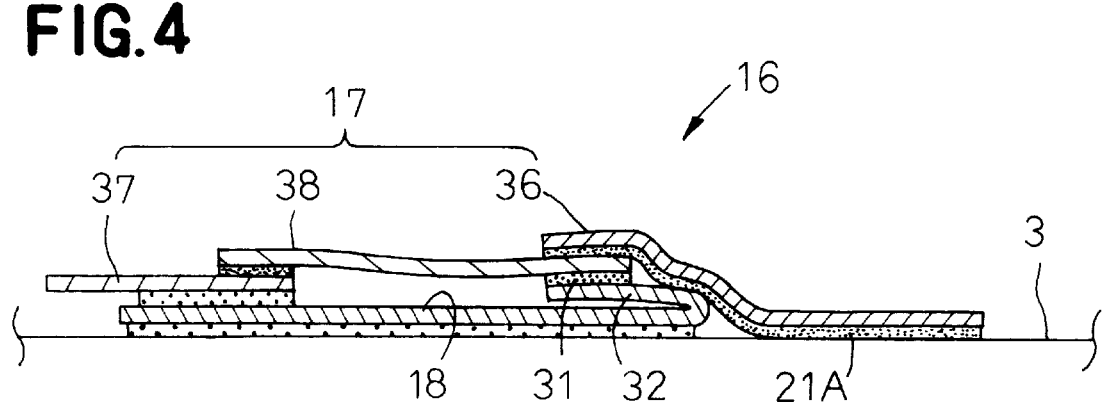
FIG. 4 is a view similar to FIG. 2, showing an embodiment of means for disposal of the used diaper.

FIG. 4 is a view similar to FIG. 2 showing another embodiment of the disposal securing means 16 according to the invention. According to this embodiment, the adhesive tape 17 forming a part of the disposal securing means 16 comprises, as viewed longitudinally of the adhesive tape 17, a backward tape 36, a forward tape 37 and a intermediate tape 38 extending between the backward and forward tapes 36, 37. The respective tapes are linearly unitized by joining them one to another at their overlapping ends. Of these tapes, the backward and forward tapes 36, 37 are made of a material which is elastic for stretch and contraction. The intermediate tape 38 is made of a material which is stretchable or somewhat elastic for stretch and contraction. In other words, the intermediate tape 38 will remain in a stretched state or elastically contract at least by a portion of the elongation after the intermediate tape 38 has been released from tension. The fold-back portion 32 of the release tape 18 is fixed to respective inner surfaces of the backward tape 36 and the intermediate tape 38 by means of adhesive 31. In this manner, the intermediate tape 38 is fixedly held between the forward lower tape 36 and the fold-back portion 32 of the release tape 18.

With the disposal securing means 16 constructed as shown in FIG. 4 also, the lower end tape 36 is also held on the diaper 1 due to the presence of the release tape 18 as in the case of the embodiment shown in FIG. 2. In addition, it is also possible for the arrangement shown in FIG. 4 to prevent the intermediate tape 38 from being peeled off from the lower end tape 36. The diaper 1 provided with such disposal securing means 16 allows the adhesive tape 17 which has been sufficiently elongated by stretching the intermediate tape 38 to be bonded to the rolled up diaper 1 at any location thereon. If the intermediate tape 38 is sufficiently stretchable, the adhesive tape 17 can be tightly wound around the rolled up diaper 1 two or even three times to make the diaper 1 less bulky. If the intermediate tape 38 is elastic not only for stretch but also for contraction, the adhesive tape 17 once having been wound around the diaper 1 will be not readily loosened.

Figure 5:
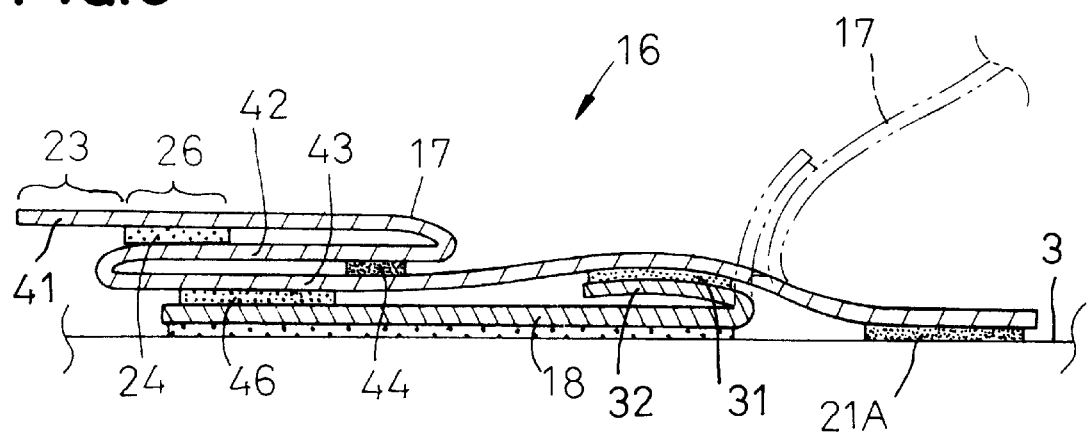
FIG. 5 is a view similar to FIG. 2, showing another embodiment of means for disposal of the used diaper.

FIG. 5 is a view similar to FIG. 2 showing still another embodiment of the disposal securing means 16. According to this embodiment, the adhesive tape 17 comprises a single piece of tape folded in a Z-shape defined by a top portion 41, an intermediate portion 42 and a bottom portion 43. The top portion 41 includes a tab zone 23 and an adhesive zone 26 applied with adhesive 24 on its inner surface. The intermediate portion 42 is releasably bonded to the bottom portion 43 by means of adhesive 44 having a relatively low adhesive strength. The bottom portion 43 is, in turn, releasably bonded to the release tape 18 by means of adhesive 46 which is also of a relatively low adhesive strength. As the adhesive tape 17 is pulled with the tab zone 23 held by the user's fingers leftward as viewed in FIG. 5, the adhesive zone 26 is peeled off from the intermediate portion 42 which is, in turn, peeled off from the bottom portion 43. The adhesive tape 17 thus unfolded and thereby elongated can be tightly wound around the used diaper 1 to secure the diaper 1 in a rolled up state. By pulling the adhesive tape 17 rightward as viewed in FIG. 5, the bottom portion 43 is peeled off from the release tape 18 and further elongated as shown by imaginary lines. This embodiment allows the adhesive tape 17 to be sufficiently elongated without use of the tape material which is elastic for stretch and contraction as used in the embodiment shown by FIG. 3.

Arrangement of the disposal securing means 16 on the diaper 1 according to the invention is not limited to the embodiments as have been described in reference with the accompanying drawings. For example, it is possible to provide the disposal securing means 16 on the front waist region 6 or the crotch region 8. It is also possible to arrange the adhesive tape 17 of the disposal securing means 16 so as to extend downward from its fixed end, instead of extending upward from its fixed end, as in the illustrated embodiments, or even to extend circumferentially around the waist regions. Furthermore, it is also possible to provide the diaper 1 with a plurality of these disposal securing means 16 at various locations on the diaper 1.

What is claimed is:

1. A disposable body fluid absorbent article comprising an inner surface intended to be placed closely adjacent a wearer's skin, an outer surface intended to be placed remotely from the wearer's skin, an absorbent core disposed between said inner surface and outer surface, and disposal securing means for securing said article in a shape desired for disposal of said article, wherein:

said disposal securing means comprise a first tape and a second tape disposed between said first tape and the outer surface of said article and extending in alignment with said first tape;

said first tape has an inner surface and an outer surface and comprises a first fixed portion adhesively directly attached on the inner surface of said first tape to the outer surface of said article and a free portion comprising a tab zone located at an end of said first tape opposite an end thereof containing said first fixed portion and having no adhesive on both the inner and outer surfaces of said tab zone, and an adhesive zone between said tab zone and first fixed portion and having adhesive only on the inner surface of said first tape;

said second tape has an inner surface and an outer surface and comprises a second fixed portion extending from said free portion toward said first fixed portion of said first tape, said second fixed portion fixed on the inner surface of said second tape to the outer surface of said article and a fold-back portion being contiguous to said second fixed portion and folded back adjacent with and away from said first fixed portion of said first tape with said inner surface of said second tape facing outward toward said first tape to define an outward facing surface; and wherein said adhesive zone provided on said free portion of said first tape is bonded to the outer surface of said second fixed portion of said second tape and said fold-back portion of said second tape is fixed on the outward facing surface of said fold-back portion to the inner surface of said free portion of said first tape.

2. The disposable body fluid absorbent article according to claim 1, wherein said first tape comprises a discrete forward tape forming said tab zone and said adhesive zone of said free portion, a discrete backward tape forming said first fixed portion and a discrete intermediate tape having a forward end and a backward end and disposed between said forward and backward tapes and being elastically stretchable, said forward tape being fixed to the forward end of said intermediate tape, the backward end of said intermediate tape being fixedly held and directly attached to and between said backward tape and said fold-back portion of said second tape.

3. The disposable body fluid absorbent article according to claim 2, wherein said intermediate tape is made of a material that will enable said intermediate tape to remain in a stretched state or elastically contract at least by a portion of elongation after said intermediate tape is released from tension following affixation to said absorbent article when soiled.

4. The disposable body fluid absorbent article according to claim 1, wherein said first tape has a longitudinal axis and is folded in a Z-shape along its longitudinal axis so as to be unfolded longitudinally in actual use thereof and said adhesive zone provided on said free portion of said first tape is releasably bonded to the outer surface of said first tape.

5. The disposable body fluid absorbent article according to claim 1, wherein said disposal securing means is provided in a center area of a rear waist region of said article.

6. The disposable body fluid absorbent article accroding to claim 5, wherein said article is a pull-on diaper.

7. The disposable article according to claim 1, wherein said first tape is a single piece of tape folded in a Z-shape defined by a top portion including said tab zone, an intermediate portion releasably bonded to a bottom surface of the top portion adjacent said tab zone, and a bottom portion functioning as a part of said free end portion of said first tape that is releasably bonded to the outer surface of said second tape with said adhesive zone and fixed directly to the fold back portion of said second tape.

* * * * *